(12) United States Patent
Ly et al.

(10) Patent No.: US 10,150,087 B2
(45) Date of Patent: Dec. 11, 2018

(54) ORGANIC SOLVENT PURIFIER AND METHOD OF USING

(71) Applicant: Entegris, Inc., Billerica, MA (US)

(72) Inventors: Saksatha Ly, Lexington, MA (US); Wai Ming Choi, West Newton, MA (US)

(73) Assignee: Entegris, Inc., Billerica, MA (US)

( * ) Notice: Subject to any disclaimer, the term of this patent is extended or adjusted under 35 U.S.C. 154(b) by 403 days.

(21) Appl. No.: 14/824,698

(22) Filed: Aug. 12, 2015

(65) Prior Publication Data

US 2015/0343391 A1 Dec. 3, 2015

Related U.S. Application Data (63) Continuation of application No. 14/397,566, filed as application No. PCT/US2013/031877 on Mar. 15, 2013, now abandoned.

(Continued)

(51) Int. Cl.
*B01D 71/32* (2006.01)
*B01D 15/00* (2006.01)
(Continued)

(52) U.S. Cl.
CPC ............. *B01D 71/32* (2013.01); *B01D 15/00* (2013.01); *B01D 15/361* (2013.01); *B01D 63/14* (2013.01);
(Continued)

(58) Field of Classification Search
CPC ........ B01D 15/08; B01D 36/00; B01D 36/16; B01D 36/1692; B01D 61/00; B01D 61/14;
(Continued)

(56) References Cited

U.S. PATENT DOCUMENTS 4,277,332 A 7/1981 Baughn
4,431,545 A 2/1984 Pall et al.
(Continued)

FOREIGN PATENT DOCUMENTS

EP 0 227 893 7/1987
EP 0 662 340 A1 7/1995
(Continued)

OTHER PUBLICATIONS

Hernandez et al., Journal of Membrane Science 112 (1996) 1-12.*
(Continued)

*Primary Examiner* — Allison G Fitzsimmons
(74) *Attorney, Agent, or Firm* — Entegris, Inc.

(57) ABSTRACT

A purifier for removing metal, such as chromium, from an organic solvent is disclosed. The purifier comprises a housing having a fluid inlet and a fluid outlet in fluid communication with the fluid inlet; a volume of ion-exchange resin disposed within the housing downstream of the fluid inlet; and a filtration member downstream of the volume of ion-exchange resin, the filtration member comprising at least one microporous membrane having a substantially neutral surface and a microporous polytetrafluoroethylene membrane downstream of the at least one microporous membrane. A method for removing metal, including chromium, from an organic solvent using a purifier of the invention is also disclosed.

28 Claims, 5 Drawing Sheets

Related U.S. Application Data (60) Provisional application No. 61/640,869, filed on May 1, 2012.

(51) Int. Cl.
    *B01D 69/12*     (2006.01)
    *B01J 47/12*     (2017.01)
    *C07C 29/76*     (2006.01)
    *B01D 63/14*     (2006.01)
    *B01D 15/36*     (2006.01)

(52) U.S. Cl.
CPC .............. *B01D 69/12* (2013.01); *B01J 47/12* (2013.01); *C07C 29/76* (2013.01); *B01D 2313/20* (2013.01); *B01D 2313/40* (2013.01); *B01D 2313/90* (2013.01); *B01D 2325/42* (2013.01)

(58) Field of Classification Search
CPC ........ B01D 63/00; B01D 63/08; B01D 69/06; B01D 69/10; B01D 69/12; B01D 71/40
USPC .................... 210/264, 265, 294, 295, 500.21
See application file for complete search history.

(56) References Cited

U.S. PATENT DOCUMENTS

| | | | |
|---|---|---|---|
| 4,618,533 | A | 10/1986 | Steuck |
| 5,681,463 | A | 10/1997 | Shimizu et al. |
| 6,103,092 | A | 8/2000 | Silva |
| 6,179,132 | B1 | 1/2001 | Moya |
| 6,379,551 | B1 | 4/2002 | Lee et al. |
| 7,172,694 | B2 | 2/2007 | Bortnick |
| 7,329,354 | B2 | 2/2008 | Mullee |
| 7,799,452 | B2 | 9/2010 | Yanagita et al. |
| 2005/0218068 | A1 | 10/2005 | Komatsu et al. |
| 2007/0007196 | A1 | 1/2007 | Komatsu |
| 2010/0044311 | A1 | 2/2010 | Kobayashi |
| 2015/0144557 | A1 | 5/2015 | Ly et al. |

FOREIGN PATENT DOCUMENTS

| | | |
|---|---|---|
| JP | 2002136968 | 5/2002 |
| WO | WO 2001/51170 | 7/2001 |
| WO | WO 2010/117845 | 10/2010 |

OTHER PUBLICATIONS

Machine Translation of Wayne et al. WO2001051170.*
Barakat, Arabian Journal of Chemistry (2011) 4, 361-377 (Year: 2011).*
Examiner's Search Report for Taiwan Application No. 102110011, "Organic Solvent Purifier and Method of Using", dated Aug. 5, 2016.
Entegris Optimizer® ST Dev Disposable Filters (Feb. 2013).
Entegris Wet Etch and Clean (Apr. 2013).
Notification of Transmittal of the International Search Report and the Written Opinion of the International Searching Authority for International Application No. PCT/US2013/031877, Organic Solvent Purifier and Method of Using, dated Oct. 6, 2013.
Notification of Transmittal the International Preliminary Report on Patentability for International Application No. PCT/US2013/031877, "Organic Solvent Purifier and Method of Using"; dated Aug. 4, 2014.
Second Written Opinion of the International Preliminary Examining Authority for International Application No. PCT/US2013/031877, "Organic Solvent Purifier and Method of Using"; dated Apr. 4, 2014.
Hernandez, A., et al., "Pore size distributions in microporous membranes. A critical analysis of the bubble point extended method", *Journal of Membrane Science*, 112 (1996) 1-12.

* cited by examiner

ORGANIC SOLVENT PURIFIER AND METHOD OF USING

RELATED APPLICATIONS

This application is a continuation of U.S. application Ser. No. 14/397,566, which is the U.S. National Stage of International Application No. PCT/US2013/031877, filed Mar. 15, 2013, which designates the U.S., published in English, and claims the benefit of U.S. Provisional Application No. 61/640,869, filed May 1, 2012. The entire teachings of these applications are incorporated herein by reference.

BACKGROUND OF THE INVENTION

Today's wet stations and spray processors require several steps to remove photoresist from a wafer. The standard wet bench configuration includes a couple of isopropyl alcohol (IPA) rinse steps, but the final rinse step, often called the IPA dry step, is a critical step. In batch applications, the final rinse is provided by a thin film of clean, distilled IPA, which condenses on the wafer surface from the vapors located above the IPA liquid. In single wafer applications, the IPA can be directly sprayed onto the wafer as a liquid. This thin layer of IPA solvent prepares the wafer for final drying.

As geometries on the wafer get increasingly smaller, the IPA dry step becomes even more critical. Critical designs are pushing towards IPA rinse only to reduce damage to wafers with extremely small pitch (line spacing), especially on gate-level applications where metal contamination is extremely critical and cannot be tolerated. Therefore, the purity of IPA plays a larger role, and making sure there are no impurities transferred to the wafer from the IPA becomes extremely important.

A low capacity version of an IPA purifier using a standard, surface-modified microporous membrane cleaned with IPA is known for low temperature and high temperature applications, but the ion-exchange capacity is very low. If severe metal spikes occurred, this filter would have difficulty with adequate capacity.

Semiconductor manufacturers purchase very clean IPA, but then transfer it through the fab and tool via stainless steel lines. This can cause the IPA to pick up iron, nickel and other trace metals from the stainless steel which, unless removed, will be deposited on the wafer during the spray application. Because these metals are present at trace levels, it is difficult to measure the amount of contamination in the fluid stream; instead, the amount of contaminant is determined as metal contamination on the wafer, typically by TXRF scans, when it has already negatively impacted gate and yield performance.

Some microporous filters have been modified with ion-exchange material and used to remove metal contaminants from deionized (DI) water. These filters show high removal of metals without selectivity to any one metal. This technology is limited because some sulfonic acid functionality can break down and be shed over time due to degradation of the ion-exchange (IEC) media. This breakdown, which has also been observed in pellet media, causes non-volatile residue (NVR) and sulfonic acid ions to shed downstream of the media. The shed residue can then be deposited on a wafer, which can be a problem for semiconductor manufacturers or end-users.

U.S. Pat. No. 7,172,694, issued Feb. 6, 2007 to Bortnik, discloses a filter assembly adapted for use in filtering fluid flow in turbomachinery. The filter assembly includes a cylindrical housing, and a filter element disposed within the housing. The housing is adapted for fluid connection to a turbomachine. The filter element is adapted to filter fluid passing to the turbomachine. The filter element includes a fluid permeable core element defining a central core element flow channel through the filter element, a fluid permeable ion exchange resin layer disposed about the core element and adapted to remove mineral and organic acids from the fluid passing through the filter element, and a pleated filter media disposed about the ion exchange resin layer and core element. In another embodiment, the filter element has the pleated filter media disposed about the core element, and the fluid permeable ion exchange resin layer disposed about the core element and pleated filter media.

There is a continuing need for a point-of-use alcohol purifier that provides higher purity solvent for a wafer spray process tool and thereby provides better semiconductor device performance and process yield.

SUMMARY OF THE INVENTION

The present invention relates to point-of-use purifiers for removing metal and, in particular, chromium from an organic solvent, for example, isopropanol, in a single pass. The purifiers of the present invention provide higher purity isopropanol for wafer spray process tools, thereby improving semiconductor device performance and overall process yield.

In one embodiment, the purifier comprises a housing having a fluid inlet and a fluid outlet in fluid communication with the fluid inlet. A volume of ion-exchange resin is disposed within the housing downstream of the fluid inlet. A filtration member is disposed downstream of the volume of ion-exchange resin and comprises at least one microporous membrane having a substantially neutral surface and a polytetrafluoroethylene (PTFE) membrane downstream of the at least one microporous membrane.

In another embodiment, the purifier comprises a cylindrical housing having a longitudinal axis, a fluid inlet and a fluid outlet in fluid communication with the fluid inlet. A volume of ion-exchange resin is disposed within the cylindrical housing downstream of the fluid inlet. The ion-exchange resin is adapted to remove metal species from the organic solvent. A pleated filtration member is disposed concentrically around the longitudinal axis within the cylindrical housing and downstream of the volume of ion-exchange resin. The pleated filtration member comprises at least one microporous membrane having a substantially neutral surface and adapted to remove chromium from the organic solvent and a microporous PTFE membrane downstream of the at least one microporous membrane.

Another embodiment of the invention is a purifier for removing metal, such as chromium, from an organic solvent. The purifier comprises a cylindrical housing having a longitudinal axis, a fluid inlet and a fluid outlet in fluid communication with the fluid inlet; a volume of ion-exchange resin disposed within the cylindrical housing downstream of the fluid inlet, the ion-exchange resin being adapted to remove metal species from the organic solvent; and a pleated filtration member disposed concentrically around the longitudinal axis within the cylindrical housing and downstream of the volume of ion-exchange resin. The pleated filtration member comprises at least three microporous membranes, each having a substantially neutral surface; and a microporous polytetrafluoroethylene ion-exchange membrane downstream of the at least three microporous membranes, wherein each microporous membrane is modified with amide and has a pore size rating greater than the pore size rating of the microporous polytetrafluoroethylene ion-exchange membrane; and the microporous polytetrafluoroethylene ion-exchange membrane has a surface modified with sulfonic acid and a pore size rating of about 1 nanometer to about 25 nanometers. Each of the at least three microporous membranes can be a microporous polytetrafluoroethylene membrane.

In addition to being able to remove chromium from an organic solvent, generally in a single pass, the purifiers of the invention can also remove other trace metals and reduce non-volatile residue in an organic solvent. Therefore, another embodiment of the invention is a method of removing metal from an organic solvent, the method comprising passing a flow of the organic solvent through a purifier described herein, thereby removing metal, such as chromium, from the organic solvent.

The benefit of a filtration member comprising a microporous PTFE membrane downstream of at least one microporous membrane having a substantially neutral surface is to capture any particles and ions that may be shed by or pass through the at least one microporous membrane, and is demonstrated by the purifier described in Example 2 herein, which can be used to remove greater than about 85% of the chromium from a solution of IPA containing 1.5 ppb chromium in a single pass (see Example 2 herein).

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

The drawings accompanying and forming part of this specification are included to depict certain aspects of the invention. A clearer impression of the invention, and of the components and operation of systems provided with the invention, will become more readily apparent by referring to the exemplary, and therefore nonlimiting, embodiments illustrated in the drawings, wherein identical reference numerals designate the same components. The features illustrated in the drawings are not necessarily drawn to scale.

DETAILED DESCRIPTION OF THE INVENTION

While various compositions and methods are described, it is to be understood that this invention is not limited to the particular molecules, compositions, designs, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "pellet" is a reference to one or more pellets, and equivalents thereof known to those skilled in the art, and so forth.

Unless defined otherwise, all technical and scientific terms used herein have the same meanings as commonly understood by one of ordinary skill in the art. Methods and materials similar or equivalent to those described herein can be used in the practice or testing of embodiments of the present invention. All publications mentioned herein are incorporated by reference in their entirety. Nothing herein is to be construed as an admission that the invention is not entitled to antedate such disclosure by virtue of prior invention. "Optional" or "optionally" means that the subsequently described event or circumstance may or may not occur, and that the description includes instances where the event occurs and instances where it does not. All numeric values herein can be modified by the term "about," whether or not explicitly indicated. The term "about" generally refers to a range of numbers that one of skill in the art would consider equivalent to the recited value (i.e., having the same function or result). In some embodiments, the term "about" refers to ±10% of the stated value; in other embodiments, the term "about" refers to ±2% of the stated value. While compositions and methods are described in terms of "comprising" various components or steps (interpreted as meaning "including, but not limited to"), the compositions and methods can also "consist essentially of" or "consist of" the various components and steps; such terminology should be interpreted as defining essentially closed or closed member groups.

One embodiment of the invention is a purifier for removing metal, such as chromium, from an organic solvent, comprising a housing having a fluid inlet and a fluid outlet in fluid communication with the fluid inlet; a volume of ion-exchange resin disposed within the housing downstream of the fluid inlet; and a filtration member downstream of the volume of ion-exchange resin and comprising at least one microporous membrane having a substantially neutral surface. In some embodiments of the invention, the filtration member further includes a microporous polytetrafluoroethylene (PTFE) membrane downstream of the at least one microporous membrane.

Figure 1:
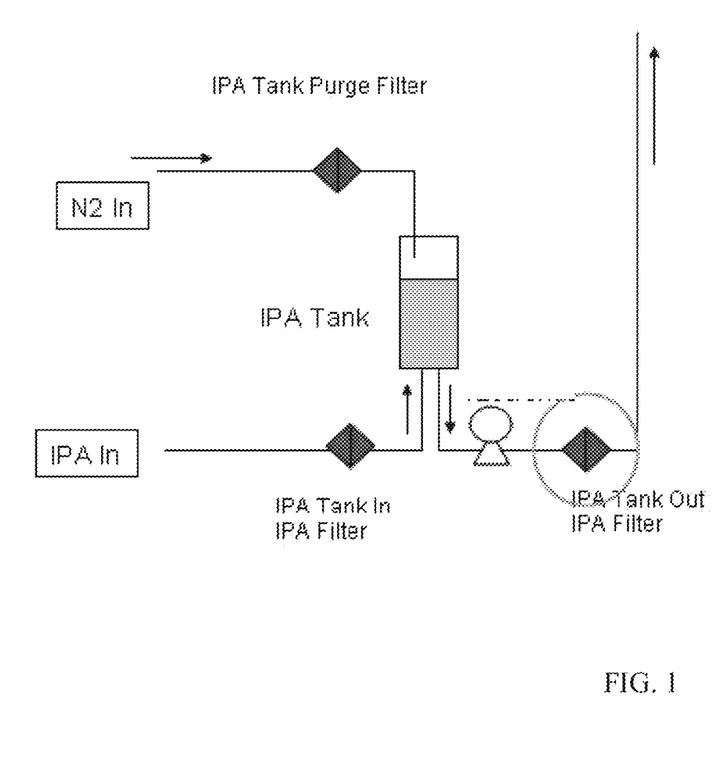
FIG. 1 shows an exemplary configuration of an IPA filter in an IPA dry process.

The purifiers of the invention can be installed within a process tool at a point-of-use (POU) application. A common set-up for an IPA dry step includes installing a purifier in a process tool or in the fluid supply pathway of IPA feeding the tool. For example, as shown in FIG. 1, a purifier of the invention can be installed at the outlet of an IPA tank and/or at the point-of-use just before the nozzle or spray tip (not shown in FIG. 1). The purifiers of the invention are particularly useful in point-of-use applications because they can remove metal and specifically, chromium, contaminants from a solvent stream in a single pass through the purifier.

The purifiers of the invention can be used to remove metal, such as chromium, from organic solvents, or mixtures of organic solvents. Organic solvents include alcohols (e.g., methanol, ethanol, isopropanol, ethyl lactate, ethylene glycol, propylene glycol monomethyl ether, cylcohexanol and mixtures thereof), polar aprotic solvents (e.g., acetonitrile, acetone, dimethylformamide, N-methyl-2-pyrrolidone, propylene glycol monomethyl ether acetate and mixtures thereof), aromatic solvents (e.g., benzene, polyarylethers, and mixtures thereof) and non-polar solvents (e.g., hexamethyldisilazane). The purifiers of the present invention can be used to purify anhydrous organic solvents or organic solvents containing some weight percentage of water (e.g., less than or equal to about 1 weight percent, less than or equal to about 0.25 weight percent, less than or equal to about 0.1 weight percent). In some embodiments of the invention, the organic solvent is an alcohol. Specifically, the alcohol is isopropanol.

Organic solvents are commonly transferred through the fab and tool via stainless steel lines. This transfer process can result in trace chromium impurities (e.g., chromium salts, chromium complexes, chromium particles) in the organic solvent. Therefore, in some embodiments, the purifier housing is plastic.

The purifiers of the invention are useful in removing chromium, including chromium salts and chromium complexes, from organic solvents, such as isopropanol. The purifier in embodiments of the invention can also remove other metal ions and complexes, such as, but not limited to, ions and complexes containing sodium, iron, aluminum, nickel, and combinations of these.

The ion-exchange resin in the purifiers of the invention is composed of particles. The particles can be thermoplastic particles that can be extruded, which is advantageous because the thermoplastic nature of the ion-exchange particles optionally allows them to be bonded to a netting or other support. Optional bonding of the ion-exchange particles to a support in some embodiments allows more uniform packing of the particles in the housing and can eliminate channeling of a fluid being purified. The ion-exchange resin can be NAFION®.

The ion-exchange particles can be non-porous and should be of a size that does not plug or reduce flow through a downstream filtration member. In addition, the ion-exchange particles should be of a size that does not pass through the microporous PTFE membrane downstream of the at least one microporous membrane. The particles, which can be in the form of pellets, beads, combinations of these, or the like, can have a size of less than about 2 millimeters. However, particles in the range of 2 mm to 0.1 mm, or 0.5 millimeters to 0.1 millimeters can also be used, depending on the pore size of the membranes in the filtration member. The ion-exchange particles can be ground. Smaller particles provide higher surface area and capacity. Particle shedding of the ion-exchange resin in versions of the invention is less than 15 particles/mL at 0.05 microns. In some embodiments of the invention, the ion-exchange resin is approximately 15 mesh to approximately 40 mesh, approximately 15 mesh to approximately 30 mesh, or approximately 15 mesh to approximately 20 mesh. Ion-exchange resins having particles of these size ranges advantageously reduce or eliminate fluid channeling through the volume of ion-exchange resin.

In some embodiments of the invention, the purifier further comprises an ion-exchange resin vessel that contains the volume of ion-exchange resin. Specifically, the ion-exchange resin vessel can comprise a net material (e.g., mesh net) or a frit (e.g., a porous frit). In this embodiment, the particles must be large enough to be retained by the net material or frit, or the pores in the net material or frit must be small enough to retain the particles. The net material or frit, as well as the volume of ion-exchange resin, should be fluid-permeable.

The filtration member is disposed downstream of the volume of ion-exchange resin and comprises at least one microporous membrane having a substantially neutral surface and a microporous PTFE membrane downstream of the at least one microporous membrane. In some embodiments, the filtration member is disposed within the housing. In some embodiments, the filtration member is disposed within the housing and upstream of the fluid outlet.

In some embodiments, the filtration member comprises more than one microporous membrane having a substantially neutral surface. The filtration member can comprise two, at least two, three, at least three, four, at least four or five microporous membranes having a substantially neutral surface.

The arrangement of the microporous membranes in the filtration member can vary. For example, in some embodiments, the at least one microporous membrane having a substantially neutral surface and the microporous PTFE membrane are disposed adjacent to one another.

Each microporous membrane can independently be a pleated flat sheet membrane, a hollow fiber, or a flat sheet membrane. In some embodiments of the invention, the at least one microporous composite membrane having a substantially neutral surface and the microporous PTFE membrane are each pleated flat sheet membranes.

The microporous membranes can further be bonded to one another. Therefore, in some embodiments of the invention, the at least one microporous membrane having a substantially neutral surface and the microporous PTFE membrane are bonded to one another. More specifically, each of the at least one microporous membranes having a substantially neutral surface and the microporous PTFE membrane are bonded to at least one of the at least one microporous membranes having a substantially neutral surface and/or the microporous PTFE membrane.

The pore size of the microporous membranes or the filtration member can be characterized by IPA bubble point or hydrofluoroether (HFE) bubble point. In some versions of the invention, a microporous membrane or filtration member can have an IPA bubble point of over about 70 pounds per square inch (psi). In some versions of the invention, a microporous membrane or filtration member can have a pore size characterized by an HFE bubble point that is 70 psi or more, or 100 psi or more. A microporous membrane or filtration member can also be characterized by its ability to remove 25 nanometer particles, and may be referred to as a 15 nanometer membrane or 10 nanometer membrane. The bubble point refers to a mean IPA bubble point using an air flow porisometer. In some cases, microporous membrane bubble points refers to a mean bubble point measured in HFE-7200 (available from 3M™, St. Paul, Minn.). HFE-7200 bubble points can be converted into IPA bubble point values by multiplying the HFE-7200 measured bubble point by 1.5, or about 1.5. 3M™ HFE-7200 is ethoxy-nonafluorobutane and has a reported surface tension of 13.6 mN/m at 25° C.

For purposes of the description and claims, the term "microporous membrane" will be used to include porous membranes that may also be described by terms such as ultraporous membranes, nanoporous membranes, and microporous membranes. These microporous membranes retain feed stream components (retentate) such as, but not limited to gels, particles, colloids, cells, and poly-oligomers, while components substantially smaller than the pores pass through the pores into a permeate steam. Retention of components in the feed stream by the microporous membrane can be dependent upon operating conditions, for example face velocity and use of surfactants, pH and combinations of these, and can be dependent upon the size and structure (hard particle or gel) of the particle relative to the size, structure and distribution of the microporous membrane pores.

In some embodiments of the invention, the microporous PTFE membrane is a microporous PTFE ion-exchange membrane, such as a phobic microporous membrane, for example, QC (QUICK CHANGE®, Entegris Inc.), including Q-1500 and Q-3000. Microporous PTFE ion-exchange membranes, and methods of making the same, are disclosed in U.S. Pat. No. 6,179,132 to Moya and in International Publication No. WO 2010/117845, the teachings of which are incorporated herein by reference in their entirety. In some embodiments of the invention, the microporous PTFE membrane has a pore size rating by bubble point of about 1 nanometer to about 100 nanometers, about 1 nanometer to about 50 nanometers, or about 1 nanometer to about 25 nanometers. In some embodiments, a surface of the microporous PTFE ion-exchange membrane is modified with sulfonic acid. Sulfonic acid-modified membranes, and methods of making the same are disclosed, for example, in International Publication No. WO 2010/117845, the teachings of which are incorporated herein by reference in their entirety.

In some embodiments, a microporous PTFE ion-exchange membrane has an ion-exchange capacity (IEC) of between about 60 nanomole/centimeter squared and about 80 nanomole/centimeter squared and/or a zeta potential of about −20 millivolts to about −30 millivolts at a pH of between about 1 and about 7.

Microporous membranes having a substantially neutral surface, and methods of making the same, are disclosed in U.S. Pat. No. 4,618,533, to Steuck, and in International Publication No. WO 01/51170, the contents of which are incorporated herein by reference in their entirety. In some embodiments of the invention, the microporous membrane having a substantially neutral surface is adapted to remove chromium (e.g., chromium salts, chromium complexes) from an organic solvent (e.g., IPA). In some embodiments of the invention, the microporous membrane having a substantially neutral surface is a microporous PTFE membrane having a substantially neutral surface, for example, a surface modified with amide groups, or a polymer comprising amide groups. Amide-modified membranes, and methods of making the same are disclosed, for example, in International Publication No. WO 01/51170, the contents of which are incorporated herein by reference in their entirety. In some embodiments of the invention, the surface of the membrane modified with amide groups advantageously also reduces the amount of non-volatile residue in the organic solvent.

A substantially neutral surface, or a weakly charged surface, is a surface having an electrostatic potential of or near 0 mV. Electrostatic potential is proportional to zeta potential. A substantially neutral surface can be formed through proper selection of a membrane material or by surface modification of a membrane. A substantially neutral surface, or weakly charged surface, can advantageously retain particles, for example, chromium particles, through non-sieving retention mechanisms. Unexpectedly, a microporous membrane having a substantially neutral surface can be used to remove chromium from isopropanol.

Non-sieving retention includes retention mechanisms, such as interception, diffusion and adsorption, that remove particles from a fluid stream without being related to the pressure drop or bubble point of the filter or microporous membrane. Particle adsorption to membrane surfaces can be mediated by, for example, intermolecular Van der Waals and electrostatic forces. Interception occurs when a particle travelling through a tortuous membrane cannot change direction fast enough to avoid contact with the membrane. Particle transport due to diffusion results from random or Brownian motion of predominantly small particles, which creates a certain probability that the particles will collide with the filter media. Non-sieving retention mechanisms can be active when there is an absence of repulsive forces between the particle and the filter or membrane.

Typically, the microporous membrane having a substantially neutral surface has a pore size rating greater than the pore size rating of the microporous PTFE membrane. The microporous membranes having a substantially neutral surface can have a particle size rating of less than or equal to about 10 μm, less than or equal to about 5 μm, less than or equal to about 1 μm, or less than or equal to about 0.5 μm. In some embodiments, the microporous membrane having a substantially neutral surface can have a particle size rating of less than or equal to about 0.2 μm, or less than or equal to about 0.1 μm.

A purifier can further include a liquid distributor downstream of the volume of ion-exchange resin and upstream of the filtration member. Typically, the liquid distributor, the ion-exchange resin and the filtration member are each disposed within the housing of the purifier. In some embodiments, the liquid distributor collects a flow of fluid from the ion-exchange resin and distributes it outwardly around the periphery of a cylindrical housing. Exemplary liquid distributor 11 collects a flow of fluid from ion-exchange resin 9 and distributes it outwardly around the periphery of cylindrical body portion 2, as illustrated in FIGS. 2 and 3.

Figure 2:
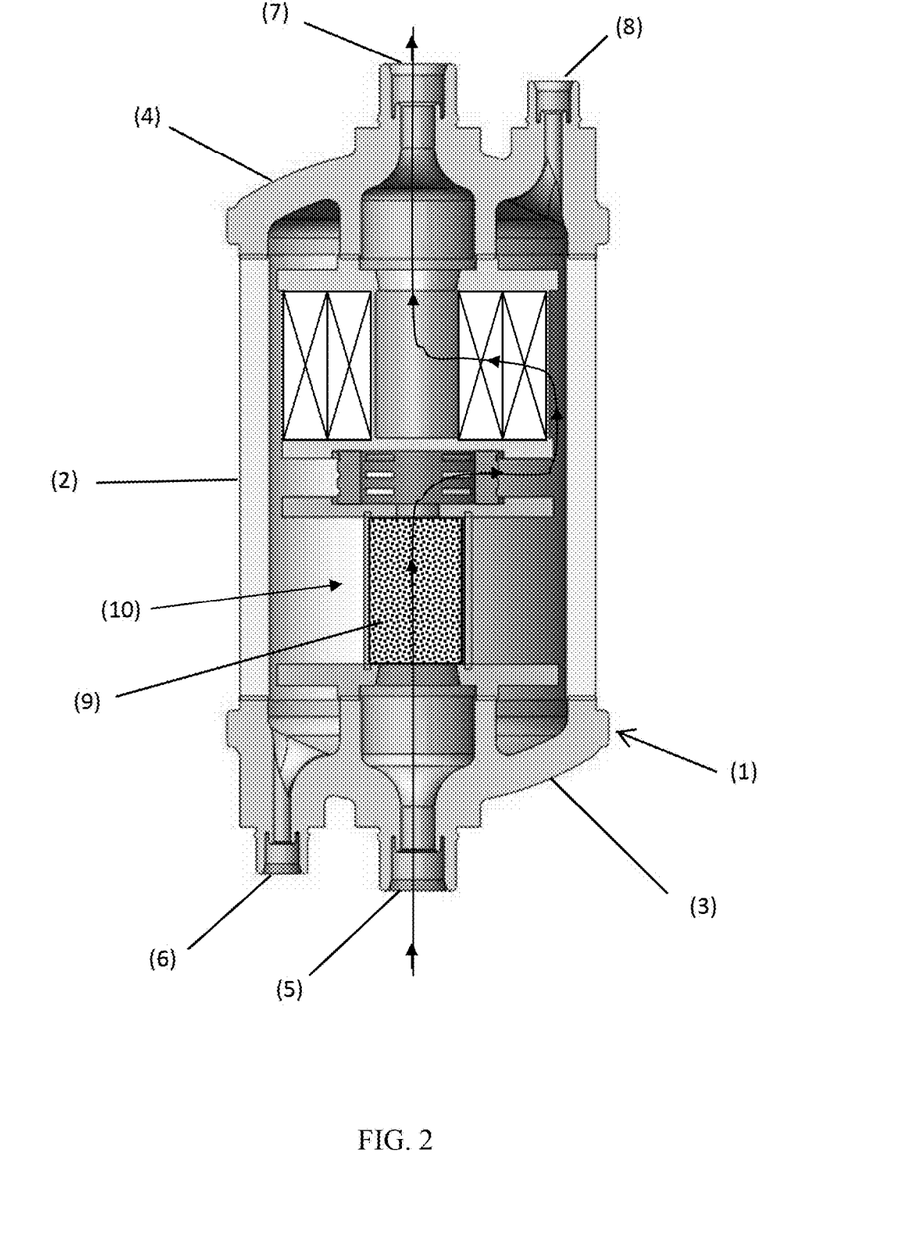
FIG. 2 is a cross-sectional view of an exemplary IPA purifier showing the fluid flow path.
Figure 3:
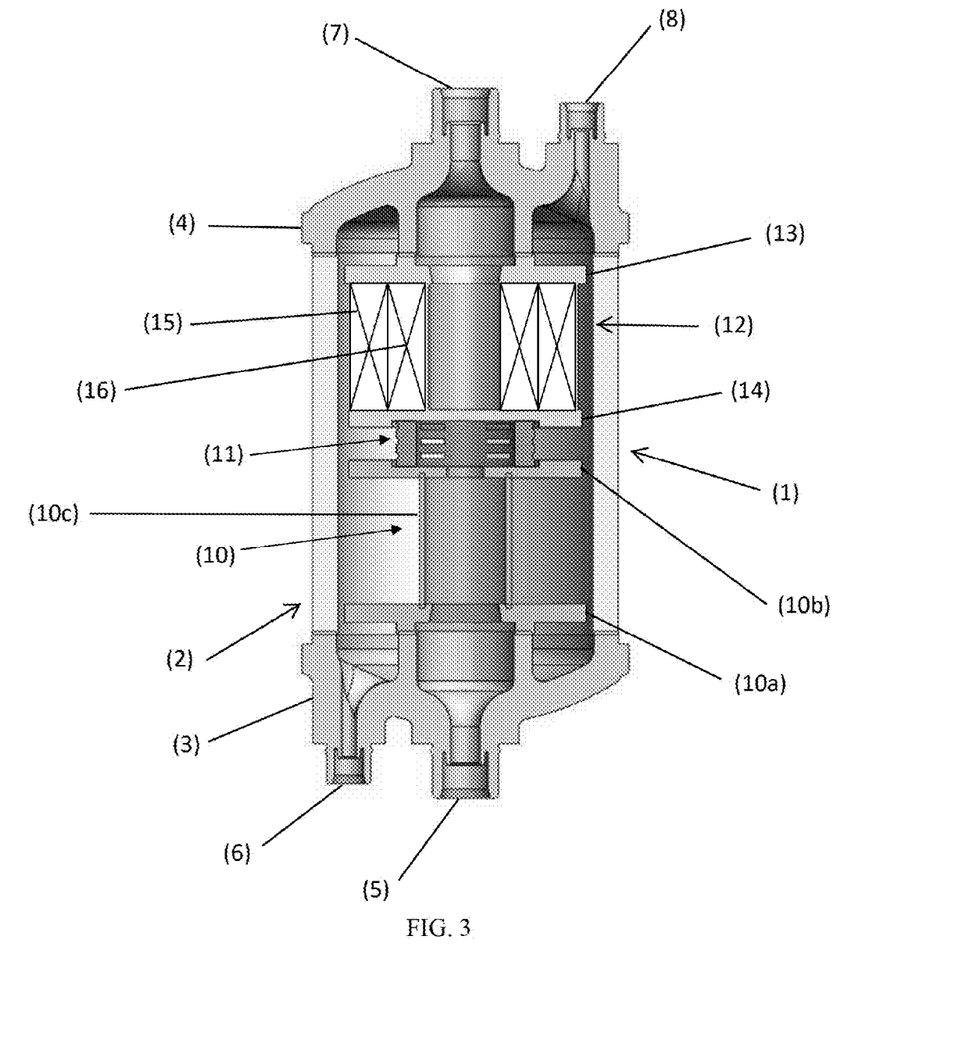
FIG. 3 is a cross-sectional view of an exemplary IPA purifier.

FIGS. 2 and 3 depict exemplary purifiers of the invention. The purifiers depicted in FIGS. 2 and 3 comprise housing 1. Housing 1 includes cylindrical body portion 2, first housing endcap 3 and second housing endcap 4. In the purifiers depicted in FIGS. 2 and 3, cylindrical body portion 2 is bonded to first and second housing endcaps 3 and 4. The housing endcaps 3 and 4 depicted in FIGS. 2 and 3 include process fluid or liquid inlet 5, drain 6, purified process fluid or liquid outlet 7 and gas vent 8. Inlet 5 and outlet 6 are in fluid communication, as indicated by the flow arrows shown in FIG. 2.

A volume of ion-exchange resin 9 is contained in ion-exchange resin vessel 10 in housing 1 in the purifiers of FIGS. 2 and 3. Ion-exchange resin vessel 10 includes bottom portion 10a which, in the purifiers depicted in FIGS. 2 and 3, is bonded to first housing endcap 3. Ion-exchange resin vessel 10 also includes top portion 10b which, in the purifiers depicted in FIGS. 2 and 3, is bonded to optional liquid distributor 11. Ion-exchange resin vessel 10 also includes cylindrical body portion 10c. Ion-exchange resin 9 is downstream of inlet 5 and upstream of optional liquid distributor 11. In some embodiments of the invention, top portion 10b and bottom portion 10a each include a frit for retaining ion-exchange resin 9 in ion-exchange resin vessel 10. In other embodiments of the invention, ion-exchange resin 9 can be retained in ion-exchange resin vessel 10 by a mesh bag.

Filter cartridge 12 is downstream of optional liquid distributor 11 in the purifiers depicted in FIGS. 2 and 3. Filter cartridge 12 includes first filter cartridge endcap 13 which, in the purifiers depicted in FIGS. 2 and 3, is bonded to second housing endcap 4. Filter cartridge 12 includes second filter cartridge endcap 14 which, in the purifiers depicted in FIGS. 2 and 3, is bonded to optional liquid distributor 11. In the purifiers depicted in FIGS. 2 and 3, filter cartridge 12 houses first filter membrane 15 and second filter membrane 16 downstream of first filter membrane 15.

In operation, the purifiers depicted in FIGS. 2 and 3 can be inserted into a fluid supply pathway feeding a process tool, such as a spray processor. Inlet 5 can be connected to a fluid supply, such as a tank (not shown), and outlet 6 can be connected to a component, such as a pipe, that feeds the fluid to a processing chamber in the tool. Fluid enters the purifier through inlet 5, flows through ion-exchange resin 9 contained in ion-exchange resin vessel 10 and enters optional liquid distributor 11. In the purifiers depicted in FIGS. 2 and 3, optional liquid distributor 11 collects a flow of fluid from ion-exchange resin 9 and distributes it outwardly around the periphery of cylindrical housing 1. The fluid then enters filter cartridge 12 and passes through first filter membrane 15, then second filter membrane 16 before flowing out of the purifier via outlet 7.

In the drawings, like elements are indicated by like reference numerals. Although FIGS. 2 and 3 depict a specific configuration of an exemplary purifier of the invention, other configurations of a purifier are possible. For example, optional liquid distributor 11 could direct a flow of fluid centrally along the longitudinal axis of housing 1, such that the fluid traverses the filters in the opposite order than that depicted in FIG. 2 (i.e., second filter membrane 16, then first filter membrane 15). Other possible modifications are known to one skilled in the art.

Another embodiment of the present inventions is a purifier for removing metal, such as chromium from an organic solvent, comprising a cylindrical housing having a longitudinal axis, a fluid inlet and a fluid outlet in fluid communication with the fluid inlet. A volume of ion-exchange resin is disposed within the cylindrical housing downstream of the fluid inlet and the ion-exchange resin is adapted to remove metal species from the organic solvent. A pleated filtration member is disposed concentrically around the longitudinal axis within the cylindrical housing and downstream of the volume of ion-exchange resin. The pleated filtration member comprises at least one microporous membrane having a substantially neutral surface and adapted to remove chromium from the organic solvent, and a microporous polytetrafluoroethylene membrane downstream of the at least one microporous membrane.

Yet another embodiment of a purifier for removing metal, such as chromium, from an organic solvent comprises a cylindrical housing having a longitudinal axis, a fluid inlet and a fluid outlet in fluid communication with the fluid inlet; a volume of ion-exchange resin disposed within the cylindrical housing downstream of the fluid inlet, the ion-exchange resin being adapted to remove metal species from the organic solvent; and a pleated filtration member disposed concentrically around the longitudinal axis within the cylindrical housing and downstream of the volume of ion-exchange resin. The pleated filtration member comprises at least three microporous membranes, each having a substantially neutral surface; and a microporous polytetrafluoroethylene ion-exchange membrane downstream of the at least three microporous membranes, wherein each microporous membrane is modified with amide and has a pore size rating greater than the pore size rating of the microporous polytetrafluoroethylene ion-exchange membrane; and the microporous polytetrafluoroethylene ion-exchange membrane has a surface modified with sulfonic acid and a pore size rating of about 1 nanometer to about 25 nanometers. Each of the at least three microporous membranes can be a microporous polytetrafluoroethylene membrane.

The invention also encompasses methods of using the purifiers of the invention. Thus, one embodiment of the invention is a method of removing metal, such as chromium, from an organic solvent using a purifier of the invention. The method comprises passing a flow of an organic solvent through a purifier of the invention, thereby removing the metal from the organic solvent. Specifically, the method comprises passing a flow of an organic solvent through a purifier of the invention one time to remove metal, including chromium, from the organic solvent.

In some embodiments, the purifier removes chromium from the organic solvent and the chromium removal is greater than about 70%, or greater than about 75% at a flow rate of about 20 mL/min, as ascertainable under the test conditions of Example 2. Specifically, the chromium removal is greater than about 80% or greater than about 85% at a flow rate of about 10 mL/min, as ascertainable under the test conditions of Example 2.

The pressure drop of the purifier, in some embodiments of the invention, is about 0.1 kgf/cm (kilogram force per centimeter) to about 0.3 kgf/cm.

EXEMPLIFICATION

Example 1

Evaluation of the Ability of an Ion-Exchange Membrane and Substantially Neutral Membranes to Remove Chromium From Isopropanol A microporous PTFE ion-exchange membrane coated with sulfonic acid functional groups and having an IEC of between about 60 nanomole/centimeter squared and about 80 nanomole/centimeter squared and a zeta potential of about −20 millivolts to about −30 millivolts at a pH of between about 1 and about 7 (sulfonic acid-modified PRS-45, a non-woven PTFE membrane having a pore size of about 20 microns) (available from Tomoegawa Inc.) and a coupon including four 0.2 µm PTFE membranes coated with amide functional groups (GUARDIAN® DEV, available from Entegris, Inc.) were challenged with a solution of isopropanol having 15 ppb chromium (from a stock solution of chromium nitrate in nitric acid) at a variety of flow rates. Each membrane was 47 mm in diameter. The challenge was continued for approximately 20 minutes at each flow rate. The concentration of chromium in the permeate stream was then measured by inductively-coupled plasma mass spectrometry (ICPMS), and the chromium removal efficiency calculated.

Figure 4:
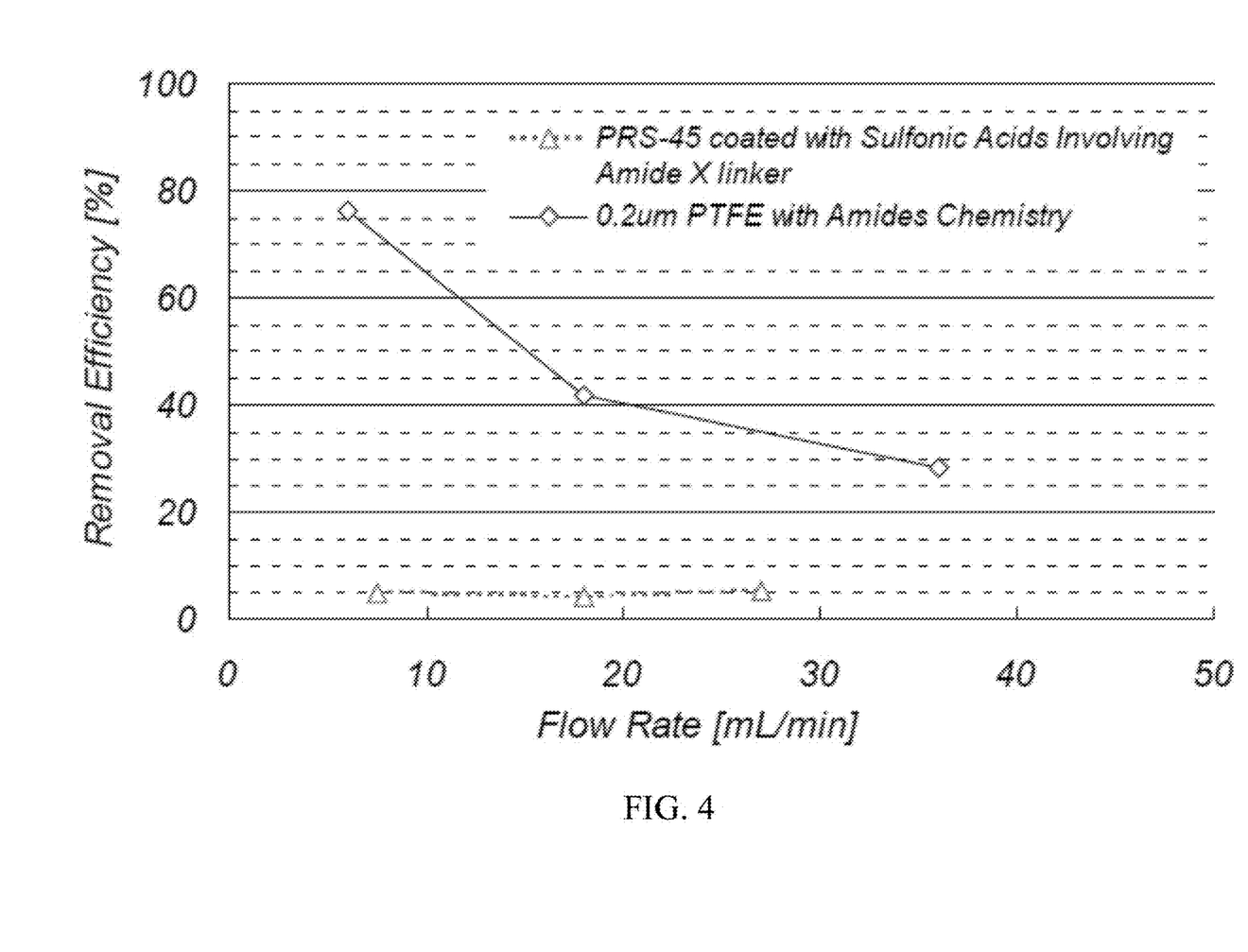
FIG. 4 is a graph of chromium removal efficiency as a function of flow rate, and shows the chromium removal efficiency from IPA of a PRS-45 membrane coated with sulfonic acids (available from Tomoegawa Inc.) and four 0.2 µm PTFE membranes coated with amides.

FIG. 4 is a graph of the chromium removal efficiency from IPA of a sulfonic acid-modified PRS-45 membrane coated with sulfonic acid functional groups and four 0.20-µm PTFE membranes coated with amides as a function of flow rate. FIG. 4 shows that the GUARDIAN® DEV membranes were very effective at removing chromium from the challenge solution, removing greater than about 75% of the chromium at a flow rate of about 8 mL/min, while the sulfonic acid-modified PRS-45 membrane was ineffective at removing chromium from the isopropanol, removing less than 5% of the chromium at all of the flow rates tested.

Example 2

Chromium Removal From IPA Using an Exemplary Purifier of the Invention

An exemplary purifier was constructed and evaluated for its ability to remove chromium from a solution of IPA containing 1.5 ppb chromium. 8 g of a pellet of an ion-exchange resin ground to 16 mesh was put into a cylindrical housing having a diameter of 47 mm. The filtration member, also disposed within the housing downstream of the ion-exchange resin, included three 0.2-µm PTFE membranes coated with amide functional groups (GUARDIAN® DEV, available from Entegris, Inc.) and a 15-nm microporous PTFE ion-exchange membrane coated with sulfonic acid functional groups (TORRENTO™, available from Entegris, Inc.) downstream of the GUARDIAN® DEV membranes.

Figure 5:
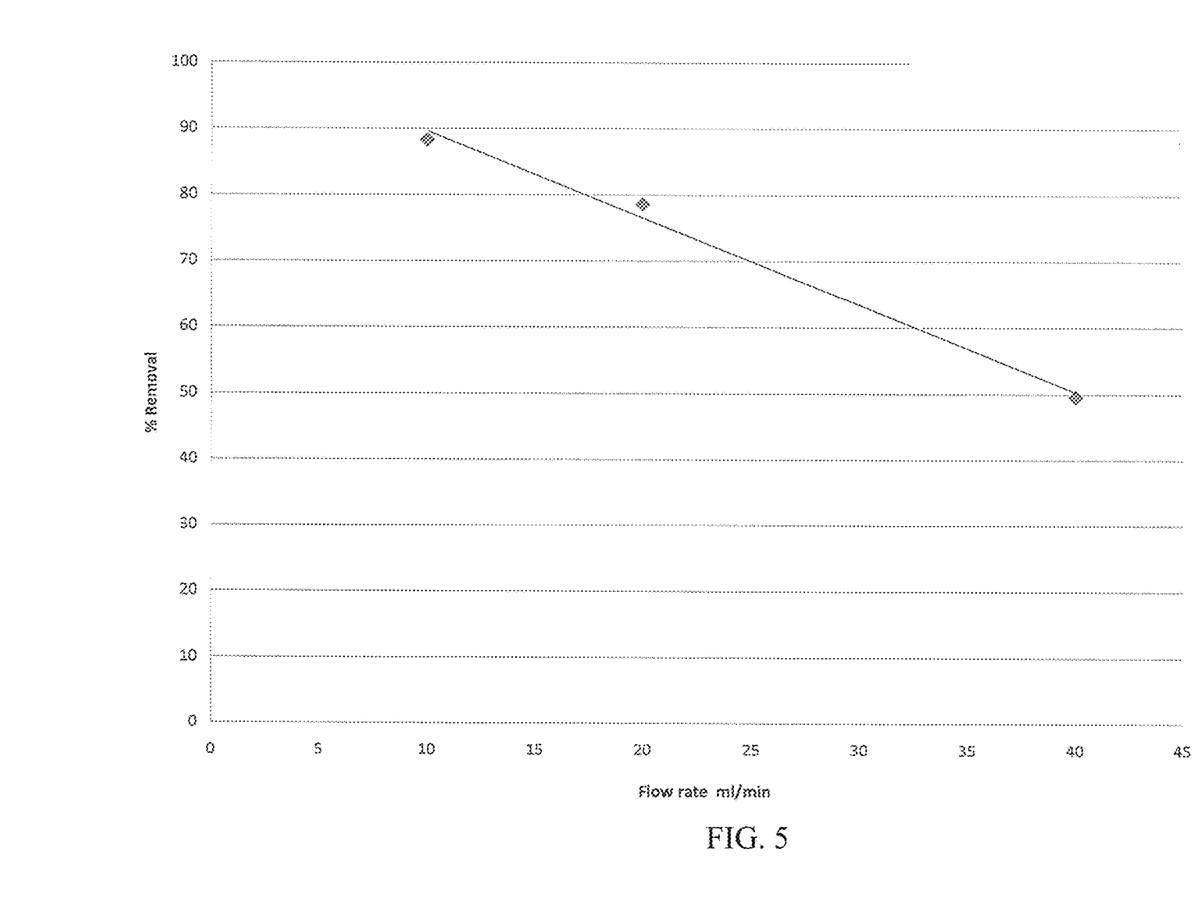
FIG. 5 is a graph of chromium removal efficiency as a function of flow rate, and shows the chromium removal efficiency from IPA of an exemplary IPA purifier of the invention, the IPA purifier described in Example 2 herein.

The purifier was challenged with a solution of isopropanol having 1.5 ppb chromium (from a stock solution of chromium nitrate in nitric acid) at a variety of flow rates. The challenge was continued for approximately 20 minutes at each flow rate. The concentration of chromium in the permeate stream was then measured by ICPMS, and the removal efficiency calculated. FIG. 5 is a graph showing the chromium removal efficiency from IPA of the purifier as a function of flow rate. FIG. 5 shows that nearly 90% of the chromium content was removed from the isopropanol in just one pass through the purifier.

Although the invention has been shown and described with respect to one or more implementations, equivalent alterations and modifications will occur to others skilled in the art based upon a reading and understanding of this specification and the annexed drawings. The invention includes all such modifications and alterations and is limited only by the scope of the following claims. In addition, while a particular feature or aspect of the invention may have been disclosed with respect to only one of several implementations, such feature or aspect may be combined with one or more other features or aspects of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising." Also, the term "exemplary" is merely meant to mean an example, rather than the best. It is also to be appreciated that features, layers and/or elements depicted herein are illustrated with particular dimensions and/or orientations relative to one another for purposes of simplicity and ease of understanding, and that the actual dimensions and/or orientations may differ substantially from that illustrated herein. Although the present invention has been described in considerable detail with reference to certain embodiments thereof, other versions are possible. Therefore the spirit and scope of the appended claims should not be limited to the description and the versions contain within this specification.

What is claimed is:

1. A purifier for removing chromium from an organic solvent, comprising:
   a housing having a fluid inlet and a fluid outlet in fluid communication with the fluid inlet;
   a volume of ion-exchange resin disposed within the housing downstream of the fluid inlet; and
   a filtration member disposed downstream of the volume of ion-exchange resin, the filtration member comprising:
      at least one amide-modified microporous polytetrafluoroethylene membrane having a substantially neutral surface with an electrostatic potential of about 0; and
      a microporous polytetrafluoroethylene ion-exchange membrane downstream of the at least one amide-modified microporous polytetrafluoroethylene membrane,
      wherein the at least one amide-modified microporous polytetrafluoroethylene membrane has a pore size rating greater than the pore size rating of the microporous polytetrafluoroethylene ion-exchange membrane and less than or equal to about 10 µm;
      and the microporous polytetrafluoroethylene ion-exchange membrane has a pore size rating by bubble point of about 1 nanometer to about 100 nanometers.

2. A purifier for removing chromium from an organic solvent, comprising:
   a cylindrical housing having a longitudinal axis, a fluid inlet and a fluid outlet in fluid communication with the fluid inlet;
   a volume of ion-exchange resin disposed within the cylindrical housing downstream of the fluid inlet; and
   a pleated filtration member disposed concentrically around the longitudinal axis within the cylindrical housing and downstream of the volume of ion-exchange resin, the pleated filtration member comprising:
      at least one amide-modified microporous polytetrafluoroethylene membrane having a substantially neutral surface with an electrostatic potential of about 0; and
      a microporous polytetrafluoroethylene ion-exchange membrane downstream of the at least one amide-modified microporous polytetrafluoroethylene membrane,
      wherein the at least one amide-modified microporous polytetrafluoroethylene membrane has a pore size rating greater than the pore size rating of the microporous polytetrafluoroethylene ion-exchange membrane and less than or equal to about 10 µm; and
      the microporous polytetrafluoroethylene ion-exchange membrane has a pore size rating by bubble point of about 1 nanometer to about 100 nanometers.

3. The purifier of claim 1, wherein a surface of the microporous polytetrafluoroethylene ion-exchange membrane is modified with sulfonic acid.

4. The purifier of claim 1, wherein the microporous polytetrafluoroethylene ion-exchange membrane has a pore size rating by bubble point of about 1 nanometer to about 50 nanometers.

5. The purifier of claim 4, wherein the microporous polytetrafluoroethylene ion-exchange membrane has a pore size rating by bubble point of about 1 nanometer to about 25 nanometers.

6. The purifier of claim 1, wherein the at least one amide-modified microporous membrane having a substantially neutral surface and the microporous polytetrafluoroethylene ion-exchange membrane are bonded to one another in the filtration member.

7. The purifier of claim 1, wherein the at least one amide-modified microporous membrane having a substantially neutral surface and the microporous polytetrafluoroethylene ion-exchange membrane are disposed adjacent to one another in the filtration member.

8. The purifier of claim 1, wherein the at least one amide-modified microporous membrane having a substantially neutral surface and the microporous polytetrafluoroethylene ion-exchange membrane are each pleated.

9. The purifier of claim 1, further comprising an ion-exchange resin vessel that contains the volume of ion-exchange resin.

10. The purifier of claim 9, wherein the ion-exchange resin vessel comprises a net material or frit.

11. The purifier of claim 1, further comprising a liquid distributor downstream of the volume of ion-exchange resin and upstream of the filtration member.

12. The purifier of claim 1, wherein the organic solvent is an alcohol.

13. The purifier of claim 12, wherein the alcohol is isopropanol.

14. The purifier of claim 1, wherein the filtration member comprises at least three amide-modified microporous polytetrafluoroethylene membranes, each having a substantially neutral surface, and the microporous polytetrafluoroethylene ion-exchange membrane is downstream of the at least three amide-modified microporous membranes.

15. A purifier for removing chromium from an organic solvent, comprising:
- a cylindrical housing having a longitudinal axis, a fluid inlet and a fluid outlet in fluid communication with the fluid inlet;
- a volume of ion-exchange resin disposed within the cylindrical housing downstream of the fluid inlet; and
- a pleated filtration member disposed concentrically around the longitudinal axis within the cylindrical housing and downstream of the volume of ion-exchange resin, the pleated filtration member comprising:
  - at least three amide-modified microporous membranes, each having a substantially neutral surface with an electrostatic potential of about 0; and
  - a microporous polytetrafluoroethylene ion-exchange membrane downstream of the at least three amide-modified microporous membranes,
  - wherein each amide-modified microporous membrane is a microporous polytetrafluoroethylene membrane modified with amide and has a pore size rating greater than the pore size rating of the microporous polytetrafluoroethylene ion-exchange membrane and less than or equal to about 10 µ; and the microporous polytetrafluoroethylene ion-exchange membrane has a surface modified with sulfonic acid and a pore size rating of about 1 nanometer to about 25 nanometers.

16. A method for removing chromium from an organic solvent, the method comprising:
- providing a flow of an organic solvent comprising chromium and
- passing the flow of the organic solvent through a purifier to thereby remove chromium from the organic solvent, the purifier comprising:
  - a housing having a fluid inlet and a fluid outlet in fluid communication with the fluid inlet;
  - a volume of ion-exchange resin disposed within the housing downstream of the fluid inlet; and
  - a filtration member disposed downstream of the volume of ion-exchange resin, the filtration member comprising:
    - at least one amide-modified microporous polytetrafluoroethylene membrane having a substantially neutral surface with an electrostatic potential of about 0; and
    - a microporous polytetrafluoroethylene ion-exchange membrane downstream of the at least one amide-modified microporous polytetrafluoroethylene membrane,
    - wherein the at least one amide-modified microporous polytetrafluoroethylene membrane has a pore size rating greater than the pore size rating of the microporous polytetrafluoroethylene ion-exchange membrane and less than or equal to about 10 µm; and the microporous polytetrafluoroethylene ion-exchange membrane has a pore size rating by bubble point of about 1 nanometer to about 100 nanometers.

17. The purifier of claim 2, wherein a surface of the microporous polytetrafluoroethylene ion-exchange membrane is modified with sulfonic acid.

18. The purifier of claim 2, wherein the microporous polytetrafluoroethylene ion-exchange membrane has a pore size rating by bubble point of about 1 nanometer to about 50 nanometers.

19. The purifier of claim 18, wherein the microporous polytetrafluoroethylene ion-exchange membrane has a pore size rating by bubble point of about 1 nanometer to about 25 nanometers.

20. The purifier of claim 2, wherein the at least one amide-modified microporous membrane having a substantially neutral surface and the microporous polytetrafluoroethylene ion-exchange membrane are bonded to one another in the filtration member.

21. The purifier of claim 2, wherein the at least one amide-modified microporous membrane having a substantially neutral surface and the microporous polytetrafluoroethylene ion-exchange membrane are disposed adjacent to one another in the filtration member.

22. The purifier of claim 2, wherein the at least one amide-modified microporous membrane having a substantially neutral surface and the microporous polytetrafluoroethylene ion-exchange membrane are each pleated.

23. The purifier of claim 2, further comprising an ion-exchange resin vessel that contains the volume of ion-exchange resin.

24. The purifier of claim 23, wherein the ion-exchange resin vessel comprises a net material or frit.

25. The purifier of claim 2, further comprising a liquid distributor downstream of the volume of ion-exchange resin and upstream of the filtration member.

26. The purifier of claim 2, wherein the organic solvent is an alcohol.

27. The purifier of claim 26, wherein the alcohol is isopropanol.

28. The purifier of claim 2, wherein the filtration member comprises at least three microporous amide-modified membranes, each having a substantially neutral surface, and the microporous polytetrafluoroethylene ion-exchange membrane is downstream of the at least three amide-modified microporous membranes.

* * * * *